United States Patent
Kawaguchi et al.

(10) Patent No.: US 6,196,843 B1
(45) Date of Patent: Mar. 6, 2001

(54) DENTAL COMPOSITION AND ARTIFICIAL TOOTH WITH THE USE OF DENTAL COMPOSITION

(75) Inventors: Satoshi Kawaguchi, Inazawa; Akira Hasegawa, Inuyama, both of (JP)

(73) Assignee: GC Dental Products Corporation, Aichi (JP)

( * ) Notice: Subject to any disclaimer, the term of this patent is extended or adjusted under 35 U.S.C. 154(b) by 0 days.

(21) Appl. No.: 09/320,138

(22) Filed: May 26, 1999

(30) Foreign Application Priority Data

May 26, 1998 (JP) .................................. 10-162929

(51) Int. Cl.[7] .................................. A61C 13/08
(52) U.S. Cl. .......................................... 433/212.1
(58) Field of Search .................. 433/202.1, 203.1, 433/212.1

(56) References Cited

U.S. PATENT DOCUMENTS

| | | |
|---|---|---|
| 4,396,377 | 8/1983 | Roemer et al. . |
| 4,396,476 | 8/1983 | Roemer et al. . |
| 4,491,453 * | 1/1985 | Koblitz et al. .................... 433/202.1 |
| 4,552,906 * | 11/1985 | Podszin et al. .................... 433/202.1 |
| 4,698,373 | 10/1987 | Tateosian et al. . |
| 5,127,834 | 7/1992 | Hasegawa et al. . |
| 5,378,737 * | 1/1995 | Jacobs et al. ..................... 433/202.1 |

* cited by examiner

Primary Examiner—Todd E. Manahan
(74) Attorney, Agent, or Firm—Wenderoth, Lind & Ponack, L.L.P.

(57) ABSTRACT

A dental composition useful for an artificial tooth and an artificial tooth with use of the said dental composition by which color stability, coloring resistance and aesthetic merit can be maintained for a long period of time and which have superior characteristics such as bending strength, impact strength, hardness and wear resistance The dental composition comprises (A) at least one monomer and/or oligomer selected from methacrylates and acrylates, (B) an uncrosslinked polymer selected from the group consisting of homopolymers of methacrylates, acrylates and styrene; copolymer of at least two monomers selected from methacrylates, acrylates and styrene; mixture of the homopolymers, mixture of the copolymers; and mixture of the homopolymer(s) and the copolymer(s), (C) a crosslinked polymer selected from the group consisting of homopolymers of methacrylates, acrylates and styrene; copolymer of at least two monomers selected from methacrylates, acrylates and styrene; mixture of the homopolymers; mixture of the copolymers; and mixture of the homopolymer(s) and the copolymer(s), (D) an organic and inorganic filler complex, and optionally (E) an inorganic filler. The said dental composition is used to make a dough, which is polymerized and molded into an artificial tooth.

24 Claims, No Drawings

DENTAL COMPOSITION AND ARTIFICIAL TOOTH WITH THE USE OF DENTAL COMPOSITION

BACKGROUND OF THE INVENTION

1. Field of the Invention

The present invention relates to a dental composition and an artificial tooth with the use of said dental composition, In more detail, the invention relates to a dental composition which has good mechanical properties and mechanical machinability, which is superior in color stability, coloring resistance and aesthetic merit, and which is suitable for an artificial tooth, as well as to an artificial tooth by the use of said dental composition.

2. Description of the Prior Art

An artificial tooth is generally required to satisfy various requirements, for example, good mechanical properties such as wear resistance, strength, and impact resistance; good mechanical machinability; good color stability and coloring resistances; superior aesthetic merit; absence of biological detrimentality; and a good biological compatibility etc.

As artificial teeth, resin teeth comprising polymethylmethacrylate as a main component, hard resin teeth comprising multifunctional methylmethacrylate and inorganic fillers, as well as porcelain teeth have been developed and are in use.

As resin teeth, those comprising methacrylate polymers and copolymers mainly consisting of methacrylate have been developed and are in use. Although those are cheap and superior in aesthetic merit, color stability and impact resistance, they have low and insufficient wear resistance. Since resin teeth are exposed to a high temperature when ground with abrasives such as carborundum point or stamp bur for occlusal adjustment by means of a laboratory machine etc., resins are molten and adhered to the abrasives, which lowers grinding efficiency extremely. Further, even though there are some differences in occlusive force during mastication of food between different persons, the force is said to correspond generally to the weight of the person. Thus, when such occlusive force being subjected to a tip of a tooth, occlusive pressure at the tip of the tooth caused by the occlusive force becomes vast. From the above-mentioned causes, there may be easily formed wear and damage in resin teeth due to occlusion during mastication or use of a tooth brush etc. Further, tooth shape may be changed by strong mastication, thus it is difficult to use it stably for a long period of time.

With a view to overcoming the defects of resin teeth; hard resin teeth have been developed Those are composite materials (composite resins) in which polymerized and hardened resins are used as matrices. The resins are prepared by kneading and dispersing inorganic fillers into multifunctional methacrylate monomers and/or oligomers. The hard resin teeth have an aesthetic merit necessary for anterior teeth and sufficient mechanical strength against occlusive pressure for molars. Further, they have preferably improved wear resistance since the inorganic fillers have high hardness. However, the inorganic fillers dispersed in the matrix resins are dug up and exposed at the surface by form-correction or polishing, or are peeled off the surface. Thus, the surface of the hard resin tooth becomes rough, resulting in deteriorated touch with the tongue. Further, dental plaque or dental calculus is deposited in voids formed by peeling of the inorganic fillers from the hard resin tooth. Thereby, the hard resin tooth may be colored. Since the multifunctional methacrylate polymer itself has poor color stability, it may be discolored during use in the mouth. Additionally, since the hard resin tooth has higher hardness than the conventional resin tooth, fractures or chips may be formed during laboratory procedures and a cusp may be easily fractured by strong mastication in the mouth.

A porcelain tooth, one kind of ceramic artificial teeth used for a long time, is high in wear resistance, excellent in aesthetic merit, color stability and coloring resistance, free from biological detrimentality or irritation in the oral condition, good in touch with the tongue, and is a stable dental material exhibiting no change in material quality even in long-term use. However, as compared with resin and hard resin teeth, it is defective in that it is high in cost, poor in elasticity, low in impact resistance because of brittleness, and tends to suffer cracking and fracture. Further, there occurs a considerable shrinkage caused by firing, thus making it difficult to accurately sinter into a prescribed shape. It is the usual practice to use a porcelain tooth after firing, polishing and form-correction. Thermal stress during correction polishing causes microcracks. And those microcracks grow larger through repetition of occlusive pressure during mastication of food and impact caused by chewing hard food, thus resulting in fatigue breakage, or under an excessive occlusion load, in breakage. When a porcelain tooth is used, mechanical retention means such as a pin or a retaining hole is provided in the porcelain tooth to achieve an integral connection of the porcelain material and the denture base resin, because of a very low adhesion between the porcelain tooth and the denture base resin serving as a denture or a support. Such retention means tends however to be subjected to stress concentration, and a defective attachment causes cracks in the surrounding denture base resin or breakage of the porcelain tooth after attachment in the mouth. The porcelain tooth may also tend to come off the denture base resin. For these reasons, manufacture of a satisfactory denture using a porcelain tooth requires skill and a high cost.

SUMMARY OF THE INVENTION

Thus, there are advantages and disadvantages in the use of resin teeth, hard resin teeth and porcelain teeth. There is therefore desired development of an artificial tooth having balanced advantages of resin teeth, hard resin teeth and porcelain teeth and also with decreased disadvantages.

The present invention was created as a result of extensive studies carried out in view of the circumstances as described above, and has an object to provide a dental composition which can maintain superior color stability, coloring resistance and aesthetic merit, which has superior characteristics in bending strength, impact strength, hardness and wear resistance etc., and which is suitable for an artificial tooth, as well as to an artificial tooth by use of said dental composition.

The foregoing and other objects, features and advantages of the present invention will become clear from the following detailed description.

DETAILED DESCRIPTION OF PREFERRED EMBODIMENTS

The dental composition and the artificial tooth according to the invention in order to accomplish the above-mentioned object are described as follows. Herein, in order to illustrate the present invention, materials used are shown as follows for convenience.

Raw material (A): at least one monomer and/or oligomer selected from methacrylates and acrylates.

Raw material (B): an uncrosslinked polymer selected from the group consisting of homopolymers of methacrylates, acrylates and styrene; copolymer of at least two monomers selected from methacrylates, acrylates and styrene; mixture of the homopolymers; mixture of the copolymers; and mixture of the homopolymer(s) and the copolymer(s).

Raw material (C): a crosslinked polymer selected from the group consisting of homopolymers of methacrylates, acrylates and styrene; copolymer of at least two monomers selected from methacrylates, acrylates and styrene, mixture of the homopolymers; mixture of the copolymers; and mixture of the homopolymer(s) and the copolymer(s).

Raw material (D): an organic and inorganic filler complex,

Raw material (E): an inorganic filler.

Therefore, the dental composition according to the invention comprises a raw material (A), a raw material (B), a raw material (C) and a raw material (D).

Thus, a dental composition which can maintain superior color stability, coloring resistance and aesthetic merit for a long period of time, which is superior in bending strength, impact strength, hardness and wear resistance etc., and which has balanced characteristics suitable for an artificial tooth is provided.

Further, the dental composition according to the invention may comprise a raw material (A), a raw material (B), a raw material (C), a raw material (D) and a raw material (E).

Thus, a dental composition which can maintain superior color stability, coloring resistance and aesthetic merit for a long period of time, and which has superior characteristics in bending strength, impact strength, hardness and wear resistance etc., suitable for an artificial tooth is provided, since the raw material (E) is cheaper than the raw material (D) and can increase hardness easily, even though some opacity may easily appear due to the material (E).

It is preferable that the crosslinked polymer is at least one of crosslinked polymers comprising polymethylmethacrylate as a main component with or without an allyl group. The raw material (A) may swell the crosslinked polymer, or may be absorbed in the crosslinked polymer, to be polymerized and hardened, by which three-dimensional interpenetrative network constitution is formed. For the crosslinked polymer comprising an allyl group, the crosslinked polymer and the polymer derived from the raw material (A) are graft-polymerized via the allyl group, to form the interpenetrative network structure. For the crosslinked polymer without an allyl group, the interpenetrative network structure is formed with the raw material (A).

Among them, increase in hardness and improvement in wear resistance may be obtained by the crosslinked polymer comprising polymethylmethacrylate as a main component without an allyl group. Further, increase in hardness as well as improvement in wear resistance and strength may be obtained by the crosslinked polymer comprising polymethylmethacrylate as a main component with an allyl group. Therefore, if both crosslinked polymers are used in together, increase in hardness as well as improvement in wear resistance and strength may be obtained.

As more concrete dental compositions, there may be exemplified a dental composition comprising a monomer and/or oligomer of methacrylate, uncrosslinked polymethylmethacrylate, at least one of crosslinked polymers comprising polymethylmethacrylate as a main component with or without an allyl group, and an organic and inorganic filler complex, as well as a composition comprising a monomer and/or oligomer of methacrylate, uncrosslinked polymethylmethacrylate, at least one of crosslinked polymers comprising polymethylmethacrylate as a main component with or without an allyl group, an organic and inorganic filler complex, and an inorganic filler.

The artificial tooth according to the invention is produced from a composition comprising a raw material (A), a raw material (B), a raw material (C) and a raw material (D) wherein a monomer and/or oligomer of the raw material (A) being polymerized and hardened.

Thus, an artificial tooth which can maintain superior color stability, coloring resistance and aesthetic merit for a long period of time, which is superior in bending strength, impact strength, hardness and wear resistance etc., and which has balanced characteristics is provided.

Further, the artificial tooth according to the invention is produced from a composition comprising a raw material (A), a raw material (B), a raw material (C), a raw material (D) and a raw material (E) wherein a monomer and/or oligomer of the raw material (A) being polymerized and hardened.

Thus, an artificial tooth which can maintain superior color stability, coloring resistance and aesthetic merit for a long period of time, and which has superior characteristics in bending strength, impact strength, hardness and wear resistance etc., is provided, since the raw material (E) is cheaper than the raw material (D) and can increase hardness easily, even though some opacity may easily appear due to the material (E).

It is preferable that the crosslinked polymer is at least one of crosslinked polymers comprising polymethylmethacrylate as a main component with or without an allyl group. The raw material (A) may swell the crosslinked polymer, or may be absorbed in the crosslinked polymer, to be polymerized and hardened, by which three-dimensional interpenetrative network constitution is formed. For The crosslinked polymer comprising an allyl group, the crosslinked polymer and the polymer derived from the raw material (A) are graft-polymerized via the allyl group, to form the interpenetrative network structure. For the crosslinked polymer without an allyl group, the interpenetrative network structure is formed with the raw material (A).

Among them, increase in hardness and improvement in wear resistance may be obtained by the crosslinked polymer comprising polymethylmethacrylate as a main component without an allyl group. Further, increase in hardness as well as improvement in wear resistance and strength may be obtained by the crosslinked polymer comprising polymethylmethacrylate as a main component with an allyl group. Therefore, if both crosslinked polymers are used in together, increase in hardness as well as improvement in wear resistance and strength may be obtained.

As more concrete artificial teeth, there may be exemplified an artificial tooth produced from a composition comprising a monomer and/or oligomer of methacrylate, uncrosslinked polymethylmethacrylate, at least one of crosslinked polymers comprising polymethylmethacrylate as a main component with (or without an allyl group, and an organic and inorganic filler complex wherein the monomer and/or oligomer of methacrylate being polymerized and hardened, as well as an artificial tooth produced from a composition comprising a monomer and/or oligomer of methacrylate, uncrosslinked polymethylmethacrylate, at least one of crosslinked polymers comprising polymethylmethacrylate as a main component with or without an allyl group, an organic and inorganic filler complex, and an inorganic filler wherein the monomer and/or oligomer of methacrylate being polymerized and hardened.

These artificial teeth have superior characteristics and have advantages of the conventional resin teeth and advantages of the hard resin teeth together and compensate for the defects of these resin and hard resin teeth. Further, they are obtained inexpensively and have superior durability.

The present invention is illustrated in more detail as follows.

As the methacrylate monomer of the raw material (A), there are exemplified methylmethacrylate, alkyl methacrylates, alicyclic, aromatic, heterocyclic and vinyl group-containing methacrylates, hydroxy(alkoxy) containing methacrylates, di and tri methacrylates, carboxylic acid containing methacrylates, dialkylaminoethyl methacrylates, fluoroalkyl methacrylates. More concretely, there are exemplified methyl methacrylate, ethyl methacrylate, n-butyl methacrylate, butyl methacrylate, t-butyl methacrylate, 2-ethylhexyl methacrylate, cyclohexyl methacrylate, benzylmethacrylate, 2-hydroxyethyl methacrylate, 2-hydroxypropyl methacrylate, dimethylaminoethyl methacrylate, diethylaminoethyl methacrylate, glycidyl methacrylate, tetrahydrofurfuryl methacrylate, ethyleneglycol dimethacrylate, 1,3-butyleneglycol dimethacrylate, diethyleneglycol dimethacrylate, triethylene glycol dimethacrylate, polyethyleneglycol dimethacrylate, 1,6-hexanediol dimethacrylate and trimethylolpropane trimethacrylate. Further, acrylates corresponding to the above-mentioned methacrylates may be exemplified. Herein, if monomers correspond to these methacrylates or acrylates, those are not limited to the above-mentioned monomers. As the raw material (A), not only monomers but also oligomers as well as mixtures of monomers and oligomers may be used.

As the raw material (B), there are exemplified homopolymers of methyl methacrylate, ethyl methacrylate, n butyl methacrylate, i-butyl methacrylate, t-butyl methacrylate, 2-ethylhexyl methacrylate, cyclohexyl methacrylate, benzylmethacrylate, 2-hydroxyethyl methacrylate, 2-hydroxypropyl methacrylate, dimethylaminoethyl methacrylate, diethylaminoethyl methacrylate, glycidyl methacrylate, tetrahydrofurfuryl methacrylate, ethyleneglycol dimethacrylate, 1,3-butyleneglycol dimethacrylate, diethyleneglycol dimethacrylate, triethylene glycol dimethacrylate, polyethyleneglycol dimethacrylate, 1,6-hexanediol dimethacrylate, trimethylolpropane trimethacrylate, homopolymers of acrylates corresponding to the above-mentioned methacrylates, homopolymers of styrene, and their copolymers, as well as mixtures of these homopolymers and copolymers. Herein, if polymers being these homopolymers of methacrylates or acrylates corresponding to the above-mentioned methacrylates or acrylates, or their copolymers, or mixtures of these homopolymers and copolymers, those are not limited to the above-mentioned substances. These may be used alone or in mixtures of two or more.

In general, the raw material (B) may be preferably used as particles. An average particle size of the raw material (B) is preferably 100 μm or less, since artificial teeth having good aesthetic merit can be obtained from said material when for example the monomer and/or oligomer of the raw material (A) being polymerized and hardened to make an artificial teeth. If the average particle size being above 100 μm, particles of the raw material (B) may appear on the surface of the artificial tooth as pearly form, which being not preferable due to lack of aesthetic merit.

The raw material (A) makes the raw material (B) swell, or the latter is made relatively dissolved or dispersed in the raw material (A). Additionally, the raw material (A) makes the crosslinked polymer of the raw material (C) to swell, by which a part of the raw material (A) is absorbed in the raw material (C). When the raw material (A) is polymerized and hardened, it forms in together with the raw material (C) an interpenetrative network structure. In the case that the dental composition comprises the raw material (A), the raw material (B), the raw material (C) and the raw material (D), the raw material (B) acts to bond the raw material (A) with the raw material (C) and the raw material (D) when the raw material (A) is polymerized and hardened. Further, in the case that the dental composition comprises the raw material (A), the raw material (B), the raw material (C), the raw material (D) and the raw material (E), the raw material (B) acts to bond the raw material (A) with the raw material (C), the raw material (D), and the raw material (E) when the raw material (A) is polymerized and hardened.

As the raw material (C), there are exemplified homopolymers of trimethylolpropane trimethylmethacrylate or its acrylates, allylmethacrylates, methyliethacrylate, ethyleneglycol di(meth)acrylate, diethyleneglycol di(meth)acrylate, triethyleneglycol di(meth)acrylate, neopentylglycol di(meth)acrylate, 1,3-butanediol di(meth)acrylate, 1,4-butanediol di(meth)acrylate, 1,6-hexanediol di(meth)acrylate, 2,2-bis(4-(meth)acryloxypolyethoxyphenyl)propane, 2,2-bis(4-(meth)acryloxypolypropoxyphenyl)propane, bis(4 (meth)-acryloxypolyethoxyphenyl)methane, 2,2-bis(4-(meth)acryloxy-diethoxyphenyl)propane, bis-(meth)acryloxyethylhydroxy isocyanurate, 2,6-bis[2'-(meth)acryloxyethyl]urethane caproic methyl, homopolymers of styrene, and their copolymers, as well as mixtures of these homopolymers and copolymers Herein, if polymers being these homopolymers of methacrylates or acrylates corresponding to the above mentioned methacrylates or acrylates, or their copolymers, or mixtures of these homopolymers and copolymers, those are not limited to the above mentioned substances. These may be used alone or in mixtures of two or more.

In general, the raw material (C) may be preferably used as particles. An average particle size of the raw material (C) is preferably 100 μm or less, since artificial teeth having good aesthetic merit can be obtained from said material when for example the monomer and/or oligomer of the raw material (A) being polymerized and hardened to make an artificial teeth. If the average particle size being above 100 μm, particles of the raw material (C) may appear on the surface of the artificial tooth as pearly form, which being not preferable due to lack of aesthetic merit.

As the inorganic filler, i.e. the raw material (E), there are exemplified quartz powders, alumina powders, silica powders, kaolin, talc, calcium carbonate, barium aluminosilicate glass, titanium oxide, borosilicate glass, colloidal silica, alumina whiskers, beryllium oxide whiskers, boron carbide whiskers, silicon carbide whiskers, silicon nitride whiskers and various metal whiskers. As an average particle size of the inorganic filler, it is preferably from 0.005 to 50 μm. If the average particle size is less than 0.005 μm, the filler becomes bulky and has quite high specific surface area. Thus, it takes a long time for uniform mixing with the raw material (B). Further, the mixture becomes too hard and difficult for making dough, by which contact with a mold becomes bad. Additionally, it is also not preferable since improvement in mechanical strength etc. being insufficient when made into an artificial tooth. If the average particle size is above 50 µm, particles become large, which makes brightness on surface insufficient, and a touch to the tongue inferior when made into an artificial tooth. Further, tooth plaque may be adhered to voids formed by peeling off of the inorganic filler or colorants of foods etc. may be adhered to them. Thereby, discoloring or coloring may be found, which being not preferable.

It is preferable that the inorganic filler is beforehand subjected to a surface treatment with a coupling agent described below.

As the organic and inorganic filler complex, i.e. the raw material (D), there are exemplified those obtained by mixing the above-mentioned inorganic filler with a methacrylate or acrylate monomer, polymerizing and then pulverizing them, As the methacrylate or acrylate monomer, there may be used any of those described in detail for the above mentioned raw material (A). As examples of the organic and inorganic filler complex, there may be used those obtained by adding the above-mentioned inorganic fillers, a methacrylate or acrylate monomer, a polymerization catalyst as described below, for example peroxides such as benzoyl peroxide, azo compounds such as azobisisobutyronitrile, a coupling agent, and optionally a colorant, an oxidation stabilizer, an ultraviolet ray absorbing agent, a pigment or a dye etc. appropriately, stirring to mix them, polymerizing them at within a range of 80 to 120° C., and then pulverizing them for example in a ball mill to an average particle size within a range of 1 to 50 µm. If the average particle size is less than 1 µm, the filler has a quite high specific surface area. Thus, it takes a long time for uniform mixing with the raw material (A). Further, the mixture becomes too hard and difficult for making dough, by which contact with a mold becomes bad. Additionally, it is also not preferable since improvement in mechanical strength etc. is insufficient when made into an artificial tooth. If the average particle size is above 50 µm, particles become large, which makes brightness on surface insufficient and a touch to a tongue inferior when made into an artificial tooth. Further, tooth plaque may be adhered to voids formed by peeling off of the inorganic filler, or colorants of foods etc. may be adhered to them. Thereby, discoloring or coloring may be found, which being not preferable. Further, there may be used those obtained by subjecting the inorganic filler beforehand to a surface treating with a coupling agent and those obtained by adding the coupling agent directly to the methacrylate or acrylate monomer and integrally blending them.

As the coupling agent, there are exemplified organofunctional silane coupling agents, coupling agents based on titanates and coupling agents based on zircoaluminates etc.

As the organofunctional silane coupling agents, there are exemplified γ-methacryloxypropyl trimethoxysilane, γ-glycidoxypropyl trimethoxysilane, vinyltrichlorosilane, vinyltriethoxysilane, N-β(aminoethyl) γ-aminopropyl trimethoxysilane, N-β(aminoethyl) γ-aminopropylmethyl dimethoxysilane, γ-chloropropyl trimethoxysilane and γ aminopropyl triethoxysilane etc.

As the coupling agents based on titanates, there are exemplified isopropyltriisostearoyl titanate,
    isopropyltridodecyl-benzenesulfonyl titanate,
    isopropyltris(dioctylpyrophosphate) titanate,
    tetraisopropylbis(dioctylphosphite) titanate,
    tetraoctylbis(ditridecylphosphite) titanate,
    tetra(2,2-diallyloxymethyl 1-butytl)bis(di-tridecyl) phosphite titanate, bis(dioctylpyrophosphate) oxyacetate titanate,
    bis(dioctyl-pyrophosphate)ethylene titanate, isopropyltrioctanoyl titanate, isopropyldimethacrylisostearoyl titanate, isopropylisostearoyl-diacryl titanate, isopropyltri (dioctylphosphate) titanate, isopropyltricumylphenyl titanate,
    isopropyltri(N-aminoethyl-aminoethlyl) titanate, dicumylphenyloxyacetate titanate and diisostearoylethylene titanate etc.

As the coupling agents based on zircoaluminates, there are exemplified alcoholic CAVCO MOD (made by CAVCO MOD: CAVEDON CHEMICAL CO., INC.), and glycolic CAVCO MOD (made by CAVCO MOD: CAVEDON CHEMICAL CO., INC.) etc.

An amount of the coupling agent added to the methacrylate or acrylate monomer is preferably from 0.1 to 25 parts by weight per 100 parts by weight of the monomer. If it is less than 0.1 parts by weight, there is not provided any effect as the coupling agent, resulting in insufficient adhesion of ultra-fine particulate filler to the above-mentioned monomer, which being not preferable. If it is above 25 parts by weight, an excess amount of the coupling agent acts as a plasticizer or defects, which being not preferable.

For the dental compositions comprising the above-mentioned raw material (A), raw material (B), raw material (C) and raw material (D) or the above-mentioned raw material (A), raw material (B), raw material (C), raw material (D) and raw material (E), it is preferable to add a polymerization catalyst in order to polymerize and harden the raw material (A).

As the polymerization catalyst, a thermal polymerization initiator is preferable. As the thermal polymerization initiator, there are exemplified organic peroxides such as benzoyl peroxide, ketone peroxide, peroxyketal, hydroperoxide, dialkyl peroxide, diacyl peroxide, peroxyester and peroxydicarbonate; and azo compounds such as
    2,2'-azobisisobutyronitrile,
    2,2'-azobis-2,4-dimethylvaleronitrile,
    4,4'-azobis-4-cyanovaleric acid,
    1,1'-azobis-1-cyclohexanecarbonitrile,
    dimethyl-2,2'-azobisisobutyrlte and
    2,2'-azobis-2-(2-aminopropane)dihydrochlorite. The thermal polymerization initiator may be used alone or in combination of two or more. An amount of the thermal polymerization initiator depends on an ability of the initiator, and it may be determined within a range of from 0.1 to 20 parts by weight per 100 parts by weight of the raw material (A). Herein, a photo-polymerization initiator etc. may be of course used as the polymerization catalyst.

Additionally, a colorant, a polymerization inhibitor, an oxidation stabilizer, an ultraviolet-ray absorbing agent, a pigment or a dye etc. may be optionally added to the raw material (A). From among, the colorant, the oxidation stabilizer, the ultraviolet-ray absorbing agent, the pigment or the dye may be added in the raw materials (B) and (C).

[Compositional proportions]

Compositional proportions of the dental composition comprising the above-mentioned raw material (A), raw material (B), raw material (C) and raw material (D) are preferable as follows; that of the raw material (A) is from 20 to 50% by weight, that of the raw material (B) is from 5 to 70% by weight, that of the raw material (C) is from 1 to 60% by weight and that of raw material (D) is from 1 to 65% by weight based on total of the raw material (A), the raw material (B), the raw material (C) and the raw material (D).

If the raw material (A) is less than 20% by weight, the powdery component may be present in excess and it cannot be made in the form of dough to obtain only dried up material, which is not preferable because of difficult moldability. If it is above 50% by weight, the liquid component may be present in excess and air bubbles may be readily formed inside, which being not preferable because of difficult moldability. From a viewpoint of molding, the desirable range is from 25 to 40% by weight.

Further, if the raw material (B) is less than 5% by weight, it cannot be made in a form of dough, which makes molding difficult. If it is above 70% by weight, the powdery component may be present in excess. Thus, it cannot be made in a form of dough to obtain dried up material, which makes molding difficult. It is therefore not preferable. From a viewpoint of molding, the desirable range is from 5 to 50% by weight.

Further, if the raw material (C) is less than 1% by weight, improvement in mechanical properties cannot be obtained, which being not preferable. If it is above 60% by the, dough property of the material is deteriorated, moldability is lowered and inside defects are produced in the molded body to lower mechanical characteristics, which is not preferable. From a viewpoint of molding and mechanical characteristics, the desirable range is from 5 to 50% by weight.

If the raw material (D) is less than 1% by weight, wear resistance, surface hardness, compressive strength and bending strength become insufficient, which is not preferable, If it is above 65% by weight, the powdery component may be present in excess or a dough property is deteriorated. Thereby, molding is made difficult, inside defects are readily produced to induce poor impact resistance, which is not preferable. From a viewpoint of molding and mechanical characteristics, the desirable range is from 5 to 60% by weight.

Further, compositional proportions of the dental composition comprising the above-mentioned raw material (A), raw material (B), raw material (C), raw material (D) and raw material (E) are preferable as follows; that of the raw material (A) is from 20 to 50% by weight, that of the raw material (B) is from 5 to 70% by weight, that of the raw material (C) is from 1 to 60% by weight, that of raw material (D) is from 1 to 65% by weight and that of raw material (E) is from 1 to 30% by weight based on total of the raw material (A), the raw material (B), the raw material (C), the raw material (D) and the raw material (E).

If the raw material (A) is less than 20% by weight, the powdery component may be present in excess, which is not preferable because of difficult moldability, and if it is above 50% by weight, the liquid component may be present in excess, which is not preferable because of difficult moldability. From a viewpoint of molding, the desirable range is from 25 to 40% by weight.

Further, if the raw material (B) is less than 5% by weight, it cannot be made in a form of dough, which makes molding difficult. If it is above 70% by weight, the powdery component may be present in excess. Thus, it cannot be made in the form of dough to obtain dried up material, which makes molding difficult. It is therefore not preferable. From a viewpoint of molding, the desirable range is from 5 to 50% by weight.

Further, if the raw material (C) is less than 1% by weight, improvement in mechanical properties cannot be obtained, which is not preferable. If it is above 60% by weight the, dough property of the material is deteriorated, moldability is lowered and inside defects are produced in the molded body to lower mechanical characteristics, which is not preferable. From a viewpoint of molding and mechanical characteristics, the desirable range is from 5 to 50% by weight.

If the raw material (D) is less than 1% by weight, wear resistance, surface hardness, compressive strength and bending strength become insufficient, which is not preferable. If it is above 65% by weight, the powdery component may be present in excess or the dough property is deteriorated. Thereby, molding is made difficult, inside defects are readily produced to induce poor impact resistance, which is not preferable. From a viewpoint of molding and mechanical characteristics, the desirable range is from 5 to 60% by weight.

If the raw material (E) is less than 1% by weight, wear resistance, surface hardness, compressive strength and bending strength become insufficient, which is not preferable. If it is above 30% by weight, the powdery component may be present in excess. Thereby, molding is made difficult, inside defects are readily produced to induce poor impact resistance, excess cloudiness is appeared to deteriorate an aesthetic merit, which is not preferable. From a viewpoint of molding, mechanical characteristics and an aesthetic merit, the desirable range is from 1 to 20% by weight.

Then, preparation of the dental composition and molding of the artificial tooth are illustrated in detail.

Herein, there is shown one example of a method for preparing raw materials and producing an artificial tooth by using said dental composition for the case of the dental composition comprising the above mentioned raw material (A), raw material (B), raw material (C) and raw material (D). At first, these raw material (A), raw material (B), raw material (C) and raw material (D) are weighed at specified compositional proportions, and then a polymerization catalyst and a coloring agent etc. are added optionally. They are mixed uniformly and allowed to make a doughy material for a specified period of time. Then, the said material is inserted into an artificial tooth mold and compressed for molding. And, the material is polymerized and molded while being pressurized in the mold. It is preferable to use a thermal polymerization initiator as the polymerization catalyst. In that case, polymerization can be carried out by heating the mold.

Also, there is shown one example of a method for preparing raw materials and producing an artificial tooth by using said dental composition for the case of the dental composition comprising the above-mentioned raw material (A), raw material (B), raw material (C), raw material (D) and raw material (E). At first, these raw material (A), raw material (B), raw material (C), raw material (D) and raw material (E) are weighed at specified compositional proportions, and then a polymerization catalyst and a coloring agent etc. are added optionally. They are mixed uniformly and allowed to make a doughy material for a specified period of time. Then, the said material is inserted into an artificial tooth mold and compressed for molding. And, the material is polymerized and molded while being pressurized in the mold. In the case that a thermal polymerization initiator being used as the polymerization catalyst, the mold is heated and polymerized.

EXAMPLES

In the following Examples, the dental compositions shown in respective examples were used to make samples, and then the thus obtained samples were evaluated for characteristics such as bending modulus, bending strength, fracture toughness, hardness and coloring resistance as evaluation items according to the following evaluating methods.

[Evaluation items and evaluating method]
<1> Bending strength, bending modulus and fracture toughness:

The tests were carried out by using a Instron Testing Machine (made by Shimazu Seisakusho, AUTOGRAPH AGS-500D) at a CHS (cross head speed)=1 mm/min and a span length=20 mm and calculating bending strength and bending modulus according to the following formula. The size of the sample was 2 mm×2 mm×25 mm.

1) Bending strength:

$$\sigma_{b3} = \frac{3PL}{2WT^2}$$

$\sigma_{b3}$ : three points bending strength (MPa)
$P$ : maximum load ($N$) at fracture of sample
$L$ : span length (mm)
$W$ : width (mm) of sample
$T$ : thickness (mm) of sample 2) Bending modulus:

$$E = \frac{L^3 P}{4WT^2 Y}$$

$E$ : bending modulus (MPa)
$L$ : span length (mm)
$P$ : load ($N$)
$W$ : width (mm) of sample
$T$ : thickness (mm) of sample
$Y$ : ratio of stress under load $P$ 3) Fracture toughness Fracture toughness is obtained by using a Instron Testing Machine (made by Shimazu Seisakusho, AUTOGRAPH AGS-500D) at a CHS (cross head speed)=1 mm/min and a span length=20 mm and calculating from an area of the determined record according to the following formula. The size of the sample was 2 mm×2 mm×25 mm.

$$E = \int \sigma \times d\varepsilon = \int \frac{3LF}{2WT^2} \cdot \frac{6T}{L^2} dl = \frac{9}{WTL}\int F dl$$

$E$ : fracture toughness (MPa)
$\sigma$ : stress (MPa)
$\varepsilon$ : strain
$F$ : load ($N$)
$l$ : deflection amount (mm)
$L$ : span length (mm)
$W$ : width (mm) of sample
$T$ : thickness (mm) of sample Herein, stress $\sigma$ is expressed by the following formula.

$$\sigma = \frac{3LF}{2WT^2}$$

Also, strain $\epsilon$ is expressed by the following formula.

$$\varepsilon = \frac{6Tl}{L^2}$$

<2> Hardness

As to hardness, micro Knoop hardness and Brinell hardness were determined.

1) Micro Knoop hardness

Micro Knoop hardness was obtained by using a micro Knoop hardness tester (made by Shimazu Seisakusho), HMV 2000 type) in a thermo-hygrostat controlled room at 23±0.5° C. and relative humidity of 50% under a load of 50 gf for a loading time of 30 seconds and calculating according to the following formula. A size of the sample was such that the diameter being 10 mm and the height was 6 mm, the sample was cylindrical $$HK = 14.23\frac{F}{d^2}$$

$HK$; micro Knoop hardness
$F$ : test load ($N$)
$d$ : length (mm) of a diagonal line of a indent, as viewed longitudinally 2) Brinell hardness Brinell hardness was obtained by using a micro-Brinell hardness tester (made by Fuji Shikenki Seisakusho, Micro-Brinell hardness tester) in a thermo-hygrostat controlled room at 23±0.5° C. and relative humidity of 50% under a load of 50 kgf for a loading time of 30 seconds and calculating according to the following formula. The size of the sample was such that the diameter being 10 mm and the height being 6 mm, wherein the sample was cylindrical.

$$HBS \text{ (or } HBW) = \frac{2F}{\pi D(D - \sqrt{D^2 - d^2})}$$

$HBS$ : Brinell hardness obtained by using a spherical indenter made of steel.
$HBW$ : Brinell hardness obtained by using a spherical indenter made of ultra-hard alloy
$F$ : test load ($N$)
$D$ : diameter of a indenter (mm)
$d$ : length (mm) of a indent <3> Coloring resistance L*, a* and b* of a sample before coloring were measured for colors by using a color computer (made by PHOTO RESEARCH, PR-650 type). The sample was dipped in a boiling aqueous solution of 0.29% basic fuchsine for 1 hour, thereafter rinsed with water, dried and measured again for color. A difference of measured data was calculated as a color difference according to the following formula, and the obtained value was used as a measure of coloring resistance.

$$\Delta E = \sqrt{(L_1^* - L_0^*)^2 + (a_1^* - a_0^*)^2 + (b_1^* - b_0^*)^2}$$

ΔE : a color difference
$L_0^*$ : $L^*$ value before coloring
$a_0^*$ : $a^*$ value before coloring
$b_0^*$ : $b^*$ value before coloring
$L_1^*$ : $L^*$ value after coloring
$a_1^*$ : $a^*$ value after coloring
$b_1^*$ : $b^*$ value after coloring Example 1

A dental composition comprised of a raw material (A), a raw material (B), a raw material (C) and a raw material (D). Concretely, the following raw materials were used.

As the raw material (A), methylmethacrylate (MMA) and ethyleneglycol dimethylmethacrylate (EDMA) were used.

As the raw material (B), polymethylmethacrylate (PMMA) having an average molecular weight of 420,000 and an average particle size of 45 μm was used.

As the raw material (C), a crosslinked polymer ① was used. The crosslinked polymer ① was a copolymer of methylmethacrylate and allylmethacrylate having allyl groups wherein an average particle size being 50 μm.

As the raw material (D), an organic and inorganic filler complex having an average particle size of 40 μm was used. The complex was prepared as follows: 100 parts by weight of fine powdery silica having an average particle size of 40 nm, 50 parts by weight of methylmethacrylate as a monomer, 6.7 parts by weight of γ-methacryloxypropyltrimethoxysilane as a coupling agent, and 0.5 parts by weight of benzoyl peroxide as a polymerization catalyst were mixed under agitation, and polymerized by heating at 90° C., and then pulverized.

As the polymerization catalyst, benzoyl peroxide was used.

The above-mentioned raw material (A), raw material (B), raw material (C), raw material (D) and the polymerization catalyst were weighed at the weight parts as shown in Table 1 of Example 1 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above-mentioned evaluating method. The results are shown in Table 1 of Example 1.

Example 2

The same raw material (A), raw material (B), raw material (C), raw material (D) and the polymerization catalyst as those used in Example 1 were weighed at the weight parts shown in Table 1 of Example 2 and mixed to homogenize, and maintained for a specified period to make a dough. The dough was put in a mold, and polymerized by heating at 135° C. and 300 MPa for 15 minutes, thereby a sample was obtained, Bending modulus, bending strength, fracture toughness, hardness and coloring resistance of the obtained samples were evaluated according to the above-mentioned evaluating method. The results are shown in Table 1 of Example 2.

Example 3

The same raw material (A), raw material (B), raw material (C), raw material (D) and the polymerization catalyst as those used in Example 1 were weighed at the weight parts shown in Table 1 of Example 3 and mixed to) homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above-mentioned evaluating method. The results are shown in Table 1 of Example 3.

Example 4

The same raw material (A), raw material (B), raw material (C), raw material (D) and the polymerization catalyst as those used in Example 1 were weighed at the weight parts shown in Table 1 of Example 4 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above-mentioned evaluating method. The results are shown in Table 1 of Example 4.

Example 5

The same raw material (A), raw material (B), raw material (C), raw material (D) and the polymerization catalyst as those used in Example 1 were weighed at the weight parts shown in Table 1 of Example 5 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture roughness, hardness and coloring resistance of the obtained samples were evaluated according to the above mentioned evaluating method. The results are shown in Table 1 of Example 5.

TABLE 1

|  | Example 1 | Example 2 | Example 3 | Example 4 | Example 5 |
| --- | --- | --- | --- | --- | --- |
| MMA * | 50 | 57 | 51 | 57 | 51 |
|  | (25.32) | (28.86) | (25.82) | (28.72) | (25.69) |
| EDMA * | 14.5 | 15.5 | 14.5 | 15.5 | 14.5 |
|  | (7.34) | (7.85) | (7.34) | (7.81) | (7.30) |
| Catalyst | 2 | 2 | 2 | 2 | 2 |
| PMMA * | 36 | 25 | 26 | 7 | 18 |
|  | (18.23) | (12.66) | (13.16) | (8.56) | (9.07) |
| Crosslinked polymer ① * | 53 | 58 | 62 | 67 | 71 |
|  | (26.84) | (29.37) | (31.39) | (33.75) | (35.77) |
| Organic and inorganic filler complex * | 44 | 42 | 44 | 42 | 44 |
|  | (22.28) | (21.27) | (22.28) | (21.16) | (22.17) |
| Inorganic filler | — | — | — | — | — |
| Bending modulus(MPa) | 3853.1 | 3602.7 | 3782.1 | 3693.3 | 3778.0 |
| Bending strength(MPa) | 102.5 | 96.9 | 97.2 | 103.3 | 96.7 |
| Fracture toughness(MPa) | 1.36 | 1.30 | 1.25 | 1.44 | 1.24 |
| Brinell hardness | 22.05 | 21.51 | 22.38 | 21.37 | 21.78 |
| Knoop hardness | 23.8 | 24.1 | 24.6 | 24.0 | 24.3 |
| Color difference ΔE | 6.31 | 6.83 | 7.02 | 6.96 | 7.11 |

Note; Figures in parentheses mean % by weight in respect to total % of those with * marks.

Example 6

The same raw material (A), raw material (B), raw material (C), raw material (D) and the polymerization catalyst as those used in Example 1 were weighed at the weight parts shown in Table 2 of Example 6 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above-mentioned evaluating method. The results are shown in Table 2 of Example 6.

Example 7

The same raw material (A), raw material (B), raw material (C), raw material (D) and the polymerization catalyst as those used in Example 1 were weighed at the weight parts shown in Table 2 of Example 7 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above mentioned evaluating method. The results are shown in Table 2 of Example 7.

The samples of Example 1 to Example 5 had intermediate characteristics between the sample consisting of the composition used for a resin tooth shown in the following Comparative Example 1 and the sample consisting of a composition used for a hard resin tooth shown in Comparative Example 2 as to bending modulus, bending strength, fracture toughness, Brinell hardness, Knoop hardness and color difference. Therefore, they can be used for making excellent artificial teeth. Additionally, the samples of Example 1 to Example 5 had particularly good transparency and they had wide coloring ranges. They are superior in aesthetic merit due to less formation of white particles formed from the inorganic filler used in the hard resin teeth and low cloudiness, and superior in coloring resistance, Although the reasons thereof are not clarified, the following matters can be considered. (i) Uniform mixing of the monomer, the uncrosslinked polymer and the crosslinked polymer is possible, since the organic and inorganic filler complex is used; (ii) the monomer is polymerized in such a state that the uncrosslinked polymer being swollen by the monomer, or the uncrosslinked polymer being relatively dissolved in the monomer, or the uncrosslinked polymer being dispersed in the monomer; (iii) an interpenetrative network structure is formed by polymerization of the monomer in such a state that the crosslinked polymer being swollen by the monomer and being penetrated into the crosslinked polymer particles, or such an interpenetrative network structure as obtained by graft reaction of the crosslinked polymer and the polymer in which a monomer being used as the raw material via a allyl group is formed; (iv) the monomer is polymerized in such a state that the polymer of methylmethacrylate used in the organic and inorganic filler complex being swollen by the monomer, or the polymer being relatively dissolved in the monomer, or the polymer being dispersed in the monomer.

The samples of Example 6 and 7 were superior in bending modulus, bending strength, fracture toughness and color difference to the sample of Comparative Example 2 consisting of the composition used for the resin tooth, and further they have similar properties for Brinell hardness and Knoop hardness to the sample of Comparative Example 2 consisting of the composition used for the hard resin tooth. However, some opaque feelings were found and color difference was relatively high compared with the samples of Example 1 to Example 5 since the content of the organic and inorganic filler complex being much, but still good. Although the reasons for these characteristics are not clarified, it is considered that the relatively low crosslinked polymer and the high content of the oraganic and inorganic filler complex effect in together act effective.

Example 8

The same raw material (A), raw material (B), raw material (C), raw material (D) and the polymerization catalyst as those used in Example 1 as well as a raw material (E) were used. An inorganic filler as the raw material (E) was obtained by coupling fine powdery silica having an average particle size of 40 nm by means of γ methacryloxypropyltrimethoxysilane as a coupling agent.

The above-mentioned raw material (A), raw material (B), raw material (C), raw material (D), raw material (E) and the polymerization catalyst were weighed at the weight parts shown in Table 2 of Example 8 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above-mentioned evaluating method. The results are shown in Table 2 of Example 8.

Example 9

The same raw material (A), raw material (B), raw material (C), raw material (D) and the polymerization catalyst as well as the raw material (E) in Example 8 were used. The raw material (A), raw material (B), raw material (C), raw material (D), raw material (E) and the polymerization catalyst were weighed at the weight parts shown in Table 2 of Example 9 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above-mentioned evaluating method. The results are shown in Table 2 of Example 9.

Example 10

The same raw material (A), raw material (B), raw material (C), raw material (D) and The polymerization catalyst as well as the raw material (E) in Example 8 were used. The raw material (A), raw material (B), raw material (C), raw material (D), raw material (E) and the polymerization catalyst were weighed at the weight parts shown in Table 2 of Example 10 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above-mentioned evaluating method, The results are shown in Table 2 of Example 10.

TABLE 2

|  | Example 6 | Example 7 | Example 8 | Example 9 | Example 10 |
|---|---|---|---|---|---|
| MMA * | 51 | 51 | 51 | 51 | 51 |
|  | (29.91) | (28.57) | (25.69) | (25.69) | (25.69) |
| EDMA * | 14.5 | 14.5 | 14.5 | 14.5 | 14.5 |
|  | (8.50) | (8.12) | (7.30) | (7.30) | (7.30) |
| Catalyst | 2 | 2 | 2 | 2 | 2 |
| PMMA * | 31.5 | 26 | 33 | 22 | 26 |
|  | (18.48) | (14.57) | (16.62) | (11.08) | (13.10) |
| Crosslinked polymer ① * | 3.5 | 7 | 78 | 89 | 62 |
|  | (2.05) | (3.92) | (39.29) | (44.84) | (31.23) |
| Organic and inorganic filler complex * | 70 | 80 | 15 | 11 | 30 |
|  | (41.06) | (44.82) | (7.56) | (5.54) | (15.11) |
| Inorganic filler * | — | — | 7 | 11 | 15 |
|  | — | — | (3.53) | (5.54) | (7.56) |
| Bending modulus(MPa) | 4423.3 | 4493.3 | 3688.2 | 3708.2 | 3821.5 |
| Bending strength(MPa) | 112.5 | 108.5 | 100.1 | 98.9 | 96.8 |
| Fracture toughness(MPa) | 1.92 | 1.66 | 1.36 | 1.32 | 1.23 |
| Brinell hardness | 26.56 | 27.12 | 21.44 | 21.51 | 22.41 |
| Knoop hardness | 27.8 | 28.4 | 22.5 | 23.8 | 24.7 |
| Color difference ΔE | 10.58 | 11.48 | 7.33 | 8.02 | 8.56 |

Note; Figures in parentheses mean % by weight in respect to total % of those with * marks.

Example 11

The same raw material (A), raw material (B), raw material (C), raw material (D) and the polymerization catalyst as well as the raw material (E) in Example 8 were used. The raw material (A), raw material (B), raw material (C), raw material (D), raw material (E) and the polymerization catalyst were weighed at the weight parts shown in Table 3 of Example 11 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above-mentioned evaluating method. The results are shown in Table 3 of Example 11.

The samples obtained in Example 8 to Example 11 had intermediate characteristics between the sample consisting of the composition used for a resin tooth shown in the following Comparative Example 1 and the sample consisting of a composition used for a hard resin tooth shown in Comparative Example 2 as to bending modulus, bending strength, fracture toughness, Brinell hardness, Knoop hardness and color. difference. Therefore, they can be used for making excellent artificial teeth. Additionally, they had good transparency and wide coloring ranges. They are superior in aesthetic merit due to less formation of white particles formed from the inorganic filler used in the hard resin teeth and low cloudiness, and superior in coloring resistance. Although the reasons thereof are not clarified, the following matters can be considered. (i) Uniform mixing of the monomer, the uncrosslinked polymer and the crosslinked polymer is possible, since the organic and inorganic filler complex is used; (ii) the monomer is polymerized in such a state that the uncrosslinked polymer being swollen by the monomer and the uncrosslinked polymer being relatively dissolved in the monomer, and the uncrosslinked polymer being dispersed in the monomer; (iii) an interpenetrative network structure is formed by polymerization of the monomer in such a state that the crosslinked polymer being swollen by the monomer and being penetrated into the crosslinked polymer particles, or such an interpenetrative network structure as obtained by graft reaction of the crosslinked polymer and the polymer in which a monomer being used as the raw material via a allyl group is formed; (iv) the monomer is polymerized in such a state that the polymer of methylmethacrylate used in the organic and inorganic filler complex being swollen by the monomer, or The polymer being relatively dissolved in the monomer, or the polymer being dispersed in the monomer. However, color difference was somewhat high and coloring resistance was slightly inferior compared to the samples obtained in Example 1 to Example 5. The reasons therefor are considered that it is caused by the organic and inorganic filler complex used together with the inorganic filler. Thus, if the filling content of the inorganic filler is increased, an opaquing trend can be found, resulting in an increased opacity. Thereby, the aesthetic merit was deteriorated somewhat.

Example 12

A dental composition composed of a raw material (A), a raw material (B), a raw material (C) and a raw material (D). Concretely, the following raw materials were used.

As the raw material (A) and the raw material (B), the same ones as in Example 1 were used.

As the raw material (C), a crosslinked polymer ② was used. The crosslinked polymer ② is polyethyleneglycol dimethacrylate comprising polymethylmethacrylate as a main component without any allyl group which has an average particle size of 50 μm.

As the raw material (D) and the polymerization catalyst, the same ones as in Example 1 were used.

The above-mentioned raw material (A), raw material (B), raw material (C), raw material (D) and the polymerization catalyst were weighed at the weight parts shown in Table 3 of Example 12 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according to the above mentioned evaluating method, The results are shown in Table 3 of Example 12.

Example 13

The same raw material (A), raw material (B), raw material (C), raw material (D) and the polymerization catalyst as those used in Example 12 were weighed at the weight parts shown in Table 3 of Example 13 and mixed to homogenize, and maintained for a specified period to make a dough. The dough was put in a mold, and polymerized by heating at 135° C. and 300 MPa for 15 minutes, thereby a sample was obtained.

Bending modulus, bending strength, fracture toughness, hardness and coloring resistance of the obtained samples were evaluated according To the above-mentioned evaluating method. The results are shown in Table 3 of Example 13.

The samples obtained in Example 12 and Example 13 had intermediate characteristics between the sample consisting of the composition used for a resin tooth shown in the following Comparative Example 1 and the sample consisting of a composition used for a hard resin tooth shown in Comparative Example 2 as to bending modulus, bending strength, fracture toughness, Brinell hardness, Knoop hardness and color difference. Therefore, they can be used for making excellent artificial teeth. Additionally, they had also good transparency and wide coloring ranges. They are superior in aesthetic merit due to less formation of white particles formed from the inorganic filler used in the hard resin teeth and low cloudiness, and superior in coloring resistance, but as to strength and hardness, they were somewhat inferior to those in Example 1 to Example 11. Although the reasons thereof are not clarified, the following matters can be considered. (i) Uniform mixing of the monomer, the uncrosslinked polymer and the crosslinked polymer is possible, since the organic and inorganic filler complex is used; (ii) the monomer is polymerized in such a state that the uncrosslinked polymer being swollen by the monomer, or the uncrosslinked polymer being relatively dissolved in the monomer, or the uncrosslinked polymer being dispersed in the monomer; (iii) an interpenetrative network structure is not formed by graft reaction of such the crosslinked polymer and the polymer in which a monomer being used as the raw material as in Example 1 to Example 11 since the crosslinked polymer does not contain an allyl group, but the monomer swells the crosslinked polymer and the monomer are polymerized in such a state that the monomer being penetrated in the crosslinked polymer particles, thus the interpenetrative network structure is formed; (iv) the monomer is polymerized in such a state that the polymer of methylmethacrylate used in the organic and inorganic filler complex being swollen by the monomer, or the polymer being relatively dissolved in the monomer, or the polymer being dispersed in the monomer

TABLE 3

|  | Example 11 | Example 12 | Example 13 |
|---|---|---|---|
| MMA * | 57 | 51 | 51 |
|  | (29.16) | (25.82) | (28.86) |
| EDMA * | 15.5 | 14.5 | 15.5 |
|  | (7.93) | (7.34) | (7.85) |
| Catalyst | 2 | 2 | 2 |
| PMMA * | 25 | 26 | 25 |
|  | (12.79) | (13.16) | (12.66) |
| Crosslinked polymer① * | 58 | — | — |
|  | (29.67) | — | — |
| Crosslinked polymer② * | — | 62 | 58 |
|  | — | (31.39) | (29.37) |
| Organic and inorganic filler complex * | 30 | 44 | 42 |
|  | (15.35) | (22.28) | (21.27) |
| Inorganic filler * | 10 | — | — |
|  | (5.12) | — | — |
| Bending modulus(MPa) | 3688.2 | 3769.5 | 3608.3 |
| Bending strength(MPa) | 97.2 | 96.8 | 96.3 |
| Fracture toughness(MPa) | 1.28 | 1.24 | 1.29 |
| Brinell hardness | 21.48 | 21.15 | 20.86 |
| Knoop hardness | 24.1 | 22.6 | 22.4 |
| Color difference ΔE | 8.43 | 7.86 | 7.43 |

Note;
Figures in parentheses mean % by weight in respect to total % of those with * marks.

Comparative Example 1

The raw material used in a resin tooth was weighed at the weight parts shown in Table 4 of Comparative Example 1 and mixed to homogenize, and maintained for a specified period to make a dough. The dough was put in a mold, and polymerized by heating at 135° C. and 300 MPa for 15 minutes, thereby a sample was obtained.

As to the thus obtained sample, the same test as in the above-mentioned Examples was carried Out.

As shown in Table 4 of Comparative Example 1, the sample had high fracture toughness and good coloring resistance (small color difference), but it had low micro Knoop hardness and Brinell hardness, which suggesting low wear resistance of resin teeth to be made.

Comparative Example 2

The raw material used in enamel segments of the hard resin tooth was weighed at the weight parts shown in Table 4 of Comparative Example 2 and mixed to homogenize, and maintained for a specified period to make a dough. The dough was put in a mold, and polymerized by heating at 135° C. and 300 MPa for 15 minutes, thereby a sample was obtained. As the inorganic filler, the same fine powdery silica as in Example 1 were used. As the organic and inorganic filler complex, the same one as in Example 1 were used.

As to the thus obtained sample, the same test as in the above-mentioned Examples was carried out.

As shown in Table 4 of Comparative Example 2, the sample was quite opposite to the sample for resin tooth. It had very high micro Knoop hardness and Brinell hardness as well as superior wear resistance, but destruction due to fracture was easily occurred since fracture toughness was very low. Further, it was very poor in coloring resistance (large color difference).

TABLE 4

|  | Comparative Example 1 | Comparative Example 2 |
|---|---|---|
| MMA | 97 | — |
| EDMA | 3 | — |
| Peroxide catalyst | 0.2 | — |
| PMMA | 200 | — |
| Urethaneacrylate | — | 30 |
| Methacrylate | — | 40 |
| Neopentylglycol dimethacrylate | — | 30 |
| Azo catalyst | — | 1 |
| Organic and inorganic filler complex | 40 | — |
| Inorganic filler | — | 9 |
| Bending modulus(MPa) | 2801.4 | 4149.6 |
| Bending strength(MPa) | 122.3 | 88.4 |
| Fracture toughness(MPa) | 2.67 | 0.94 |
| Brinell hardness | 18.35 | 27.95 |
| Knoop hardness | 18.2 | 35.8 |
| Color difference ΔE | 9.11 | 31.10 |

The dental composition according to the invention comprises the monomer and/or oligomer, the uncrosslinked polymer, the crosslinked polymer, the organic and inorganic filler complex, and optionally the inorganic filler. It was prepared by utilizing swelling and dissolution of the uncrosslinked polymer by means of the monomer and/or oligomer as well as swelling of the crosslinked polymer etc, to polymerize the monomer and/or oligomer and form an interpenetrative network structure. By using the dental composition according to the invention for making an artificial tooth etc., there can be provided an artificial tooth at cheap cost by wherein color stability and coloring resistance as well as an aesthetic merit can be maintained for a long period. It has superior characteristics such as bending strength, impact strength, hardness and wear resistance, has both advantages of the conventional resin tooth and the hard resin tooth, and it also supplements the defects of the resin tooth and the hard resin tooth.

For example, the artificial tooth with use of the dental composition according to the invention has higher hardness than the conventional resin tooth but has lower hardness characteristics than those of tile hard resin tooth and the porcelain tooth. Thereby, low wear resistance of the resin tooth and low fracture toughness of the hard resin tooth and the porcelain tooth can be improved. Further, color stability and coloring resistance are much superior to those of the hard resin tooth, an aesthetic merit ii equal to those of resin tooth and the porcelain tooth. Thus, the artificial tooth according to the invention is quite useful. Additionally, the dental composition is obtained at a low cost, since the raw materials thereof are cheap and preparation is easy. Thus, cheap and good qualities can be provided, since production of the artificial tooth is easy.

More concretely, by a dental composition comprising (A) at least one monomer and/or oligomer selected from methacrylates and acrylates, (B) an uncrosslinked polymer selected from the group consisting of homopolymers of methacrylates, acrylates and styrene; copolymer of at least two monomers selected from methacrylates, acrylates and styrene; mixture of the homopolymers; mixture of the copolymers; and mixture of the homopolymer(s) and the copolymer(s), (C) a crosslinked polymer selected from the group consisting of homopolymers of methacrylates, acrylates and styrene; copolymer of at least two monomers selected from methacrylates, acrylates and styrene; mixture of the homopolymers; mixture of the copolymers, and mixture of the homopolymer(s) and the copolymer(s), and (D) an organic and inorganic filler complex, there can be provided a dental composition useful for an artificial tooth in which color stability, coloring resistance and aesthetic merit can be maintained for a long period of time, which is superior in bending strength, impact strength, hardness and wear resistance etc. and which has balanced characteristics.

The artificial tooth obtained by using said dental composition can maintain color stability, coloring resistance and aesthetic merit for a long period of time, is superior in bending strength, impact strength, hardness and wear resistance etc. and has balanced characteristics, since the composition comprising the raw material (A), the raw material (B), the raw material (C) and the raw material (D) is made by polymerizing and hardening the monomer and/or the oligomer in (A).

Further, by a dental composition comprising (A) at least one monomer and/or oligomer selected from methacrylates and acrylates, (B) an uncrosslinked polymer selected from the group consisting of homopolymers of methacrylates, acrylates and styrene; copolymer of at least two monomers selected from methacrylates, acrylates and styrene; mixture of the homopolymers; mixture of the copolymers; and mixture of the homopolymer(s) and the copolymer(s), (C) a crosslinked polymer selected from the group consisting of homopolymers of methacrylates, acrylates and styrene; copolymer of at least two monomers selected from methacrylates, acrylates and styrene; mixture of the homopolymers; mixture of the copolymers; and mixture of the homopolymer(s) and the copolymer(s), (D) an organic and inorganic filler complex, and (E) an inorganic filler, there can be provided a dental composition useful for an artificial tooth in which a color stability, a coloring resistance and an aesthetic merit can be maintained for a long period of time, which is superior in bending strength, impact strength, hardness and wear resistance etc. and which has balanced characteristics even though with a somewhat opaqueness due to the raw material (E). Herein, the raw material (E) is inexpensive compared to the raw material (D) and the former has a tendency to raise hardness etc.

The artificial tooth obtained by using said dental composition can maintain color stability, coloring resistance and aesthetic merit for a long period of time, is superior in bending strength, impact strength, hardness and wear resistance etc, and has balanced characteristics even though with a somewhat opaqueness due to the raw material (E), since the composition comprising the raw material (A), the raw material (B), the raw material (C), the raw material (D) and the raw material (E) is made by polymerizing and hardening the monomer and/or the oligomer in (A). Herein, the raw material (E) is inexpensive compared to the raw material (D) and the former has a tendency to raise hardness etc.

It is preferable that the crosslinked polymer is at least one of crosslinked polymers comprising polymethylmethacrylate as a main component with or without an allyl group. The raw material (A) may swell the crosslinked polymer, or may be absorbed in the crosslinked polymer, to be polymerized and hardened, by which three-dimensional interpenetrative network constitution is formed. For the crosslinked polymer comprising an allyl group, the crosslinked polymer and the polymer derived from the raw material (A) are graft polymerized via the allyl group, to form the interpenetrative network structure. For the crosslinked polymer without an allyl group, the interpenetrative network structure is formed with the raw material (A).

Among them, increase in hardness and improvement in wear resistance may be obtained by the crosslinked polymer comprising polymethylmethacrylate as a main component without an allyl group. Further, increase in hardness as well as improvement in wear resistance and strength may be obtained by the crosslinked polymer comprising polymethylmethacrylate as a main component with an allyl group. Therefore, if both crosslinked polymers are used in together, increase in hardness as well as improvement in wear resistance and strength may be obtained.

Needless to mention, the present invention is not limited by the foregoing examples.

What is claimed is:

1. A dental composition comprising:
   (A) at least one monomer and/or oligomer selected from the group consisting of methacrylates and acrylates,
   (B) an uncrosslinked polymer selected from the group consisting of homopolymers of methacrylates, acrylates and styrene; copolymer of at least two monomers selected from the group consisting of methacrylates, acrylates and styrene; mixture of the homopolymers; mixture of the copolymers; and mixture of the homopolymer(s) and the copolymer(s),
   (C) a crosslinked polymer selected from the group consisting of homopolymers of methacrylates, acrylates and styrene; copolymer of at least two monomers selected from the group consisting of methacrylates, acrylates and styrene; mixture of the homopolymers; mixture of the copolymers; and mixture of the homopolymer(s) and the copolymer(s), and
   (D) an organic and inorganic filler complex produced by a process comprising admixing powdered inorganic filler with a methacrylate or acrylate monomer, polymerizing said monomer and then pulverizing the resultant product.

2. The dental composition according to claim 1 wherein said crosslinked polymer is at least one of crosslinked polymers comprising polymethylmethacrylate as a main component with or without an allyl group.

3. The dental composition according to claim 1 wherein said organic and inorganic filler complex has an average particle size of 1 to 50 μm.

4. The dental composition according to claim 1 wherein said monomer and/or oligomer is present in an amount of from 20 to 50% by weight, said uncrosslinked polymer is present in an amount of from 5 to 70% by weight, said crosslinked polymer is present in an amount of from 1 to 60% by weight, and said organic and inorganic filler complex is present in an amount of from 1 to 65% by weight.

5. A dental composition comprising a monomer and/or oligomer of methacrylate, uncrosslinked polymethylmethacrylate, at least one of crosslinked polymers comprising polymethylmethacrylate as a main component with or without an allyl group, and an organic and inorganic filler complex produced by a process comprising admixing powdered inorganic filler with a methacrylate or acrylate monomer, polymerizing said monomer and then pulverizing the resultant product.

6. The dental composition according to claim 5, wherein said organic and inorganic filler complex has an average particle size of 1 to 50 μm.

7. An artificial tooth produced from a composition comprising:
   (A) at least one monomer and/or oligomer selected from the group consisting of methacrylates and acrylates,
   (B) an uncrosslinked polymer selected from the group consisting of homopolymers of methacrylates, acrylates and styrene; copolymer of at least two monomers selected from methacrylates, acrylates and styrene; mixture of the homopolymers; mixture of the copolymers; and mixture of the homopolymer(s) and the copolymer(s),
   (C) a crosslinked polymer selected from the group consisting of homopolymers of methacrylates, acrylates and styrene; copolymer of at least two monomers selected from methacrylates, acrylates and styrene; mixture of the homopolymers, mixture of the copolymers; and mixture of the homopolymer(s) and the copolymer(s); and
   (D) an organic and inorganic filler complex produced by a process comprising admixing powdered inorganic filler with a methacrylate or acrylate monomer, polymerizing said monomer and then pulverizing the resultant product, wherein a monomer and/or oligomer (A) are polymerized and hardened.

8. The artificial tooth according to claim 7 wherein said crosslinked polymer is at least one of crosslinked polymers comprising polymethylmethacrylate as a main component with or without an allyl group.

9. The artificial tooth according to claim 7 wherein said organic and inorganic filler complex has an average particle size of 1 to 50 μm.

10. The artificial tooth according to claim 7 wherein said monomer and/or oligomer is present in an amount of from 20 to 50% by weight, said uncrosslinked polymer is present in an amount of from 5 to 70% by weight, said crosslinked polymer is present in an amount of from 1 to 60% by weight, and said organic and inorganic filler complex is present in an amount of from 1 to 65% by weight.

11. An artificial tooth produced from a composition comprising a monomer and/or oligomer of methacrylate, uncrosslinked polymethylmethacrylate, at least one of crosslinked polymers comprising polymethylmethacrylate as a main component with or without an allyl group, and an organic and inorganic filler complex produced by a process comprising admixing powdered inorganic filler with a methacrylate or acrylate monomer, polymerizing said monomer and then pulverizing the resultant product, wherein said monomer and/or oligomer of methacrylate are polymerized and hardened.

12. The artificial tooth according to claim 11 wherein said organic and inorganic filler complex has an average particle size of 1 to 50 μm.

13. A dental composition comprising:
   (A) at least one monomer and/or oligomer selected from the group consisting of methacrylates and acrylates,
   (B) an uncrosslinked polymer selected from the group consisting of homopolymers of methacrylates, acrylates and styrene; copolymer of at least two monomers selected from methacrylates, acrylates and styrene; mixture of the homopolymers; mixture of the copolymers; and mixture of the homopolymer(s) and the copolymer(s),
   (C) a crosslinked polymer selected from the group consisting of homopolymers of methacrylates, acrylates and styrene; copolymer of at least two monomers selected from the group consisting of methacrylates, acrylates and styrene; mixture of the homopolymers; mixture of the copolymers; and mixture of the homopolymer(s) and the copolymer(s),
   (D) an organic and inorganic filler complex produced by a process comprising admixing powdered inorganic filler with a methacrylate or acrylate monomer, polymerizing said monomer and then pulverizing the resultant product, and
   (E) an inorganic filler.

14. The dental composition according to claim 13 wherein said organic and inorganic filler complex has an average particle size of 1 to 50 μm.

15. The dental composition according to claim 13 wherein said crosslinked polymer is at least one of crosslinked polymers comprising polymethylmethacrylate as a main component with or without an allyl group.

16. The dental composition according to claim 13 wherein said monomer and/or oligomer is present in an amount of from 20 to 50% by weight, said uncrosslinked polymer is present in an amount of from 5 to 70% by weight, said crosslinked polymer is present in an amount of from 1 to 60% by weight, said organic and inorganic filler complex is present in an amount of from 1 to 65% by weight and said inorganic filler is present in an amount of from 1 to 30% by weight.

17. A dental composition comprising a monomer and/or oligomer of methacrylate, uncrosslinked polymethylmethacrylate, at least one of crosslinked polymers comprising polymethylmethacrylate as a main component with or without an allyl group, an organic and inorganic filler complex produced by a process comprising admixing powdered inorganic filler with a methacrylate or acrylate monomer, polymerizing said monomer and then pulverizing the resultant product, and an inorganic filler.

18. The dental composition according to claim 17 herein said organic and inorganic filler complex has an average particle size of 1 to 50 μm.

19. An artificial tooth produced from a composition comprising:
   (A) at least one monomer and/or oligomer selected from the group consisting of methacrylates and acrylates,
   (B) an uncrosslinked polymer selected from the group consisting of homopolymers of methacrylates, acrylates and styrene; copolymer of at least two monomers selected from methacrylates, acrylates and styrene; mixture of the homopolymers; mixture of the copolymers; and mixture of the homopolymer(s) and the copolymer(s),
   (C) a crosslinked polymer selected from the group consisting of homopolymers of methacrylates, acrylates and styrene; copolymer of at least two monomers selected from methacrylates, acrylates and styrene; mixture of the homopolymers; mixture of the copolymers; and mixture of the homopolymer(s) and the copolymer(s),
   (D) an organic and inorganic filler complex produced by a process comprising admixing powdered inorganic filler with a methacrylate or acrylate monomer, polymerizing said monomer and then pulverizing the resultant product, and (E) an inorganic filler,
wherein said monomer and/or oligomer (A) are polymerized and hardened.

20. The artificial tooth according to claim 19 wherein said crosslinked polymer is at least one of crosslinked polymers comprising polymethylmethacrylate as a main component with or without an allyl group.

21. The artificial tooth according to claim 19 wherein said organic and inorganic filler complex has an average particle size of 1 to 50 μm.

22. The artificial tooth according to claim 19 wherein said monomer and/or oligomer is present in an amount of from 20 to 50% by weight, said uncrosslinked polymer is present in an amount of from 5 to 70% by weight, said crosslinked polymer is present in an amount of from 1 to 60% by weight, said organic and inorganic filler complex is present in an amount of from 1 to 65% by weight, and said inorganic filler is present in an amount of from 1 to 30% by weight.

23. An artificial tooth produced from a composition comprising a monomer and/or oligomer of methacrylate, uncrosslinked polymethylmethacrylate, at least one of crosslinked polymers comprising polymethylmethacrylate as a main component with or without an allyl group, an organic and inorganic filler complex produced by a process comprising admixing powdered inorganic filler with a methacrylate or acrylate monomer, polymerizing said monomer and then pulverizing the resultant product, and an inorganic filler, wherein said monomer and/or oligomer of methacrylate are polymerized and hardened.

24. The artificial tooth according to claim 23 wherein said organic and inorganic filler complex has an average particle size of 1 to 50 μm.

* * * * *